US007901912B1

(12) United States Patent
Okuyama et al.

(10) Patent No.: US 7,901,912 B1
(45) Date of Patent: Mar. 8, 2011

(54) METHOD OF PRODUCING URIDINE 5'-DIPHOSPHO-N-ACETYLGALACTOSAMINE

(75) Inventors: Kiyoshi Okuyama, Chiba (JP); Toshitada Noguchi, Chiba (JP)

(73) Assignee: Yamasa Corporation, Chiba (JP)

( * ) Notice: Subject to any disclaimer, the term of this patent is extended or adjusted under 35 U.S.C. 154(b) by 310 days.

(21) Appl. No.: 11/576,837

(22) PCT Filed: Oct. 18, 2005

(86) PCT No.: PCT/JP2005/019081
§ 371 (c)(1),
(2), (4) Date: Apr. 6, 2007

(87) PCT Pub. No.: WO2006/043525
PCT Pub. Date: Apr. 27, 2006

(30) Foreign Application Priority Data

Oct. 21, 2004 (JP) .................................. 2004-306783

(51) Int. Cl.
| | |
|---|---|
| C12P 19/00 | (2006.01) |
| C12P 19/26 | (2006.01) |
| C12P 19/30 | (2006.01) |
| C12P 21/06 | (2006.01) |
| C12N 9/10 | (2006.01) |
| C12N 9/12 | (2006.01) |
| C12N 9/00 | (2006.01) |
| C07H 21/04 | (2006.01) |
| C08B 37/00 | (2006.01) |

(52) U.S. Cl. .............. 435/72; 435/84; 435/89; 435/69.7; 435/193; 435/194; 435/183; 536/23.2; 536/23.4; 536/53

(58) Field of Classification Search ..................... 435/72, 435/84, 89, 69.7, 193, 194, 183; 536/23.2, 536/23.4, 53
See application file for complete search history.

(56) References Cited

U.S. PATENT DOCUMENTS

| 5,516,665 A | * | 5/1996 | Wong | .............................. 435/97 |
| 2003/0180928 A1 | * | 9/2003 | Gilbert et al. | ................. 435/193 |

FOREIGN PATENT DOCUMENTS

| WO | 99/11810 | 3/1999 |
| WO | 02/50267 | 6/2002 |

OTHER PUBLICATIONS

Bourgeaux et al., Two-step enzymatic synthesis of UDP-N-acetylgalactosamine. Bioorg. Med. Chem. Lett., 2005, vol. 15: 5459-5462.*
Broun et al., Catalytic plasticity of fatty acid modification enzymes underlying chemical diversity of plant lipids. Science, 1998, vol. 282: 1315-1317.*
Kisselev L., Polypeptide release factors in prokaryotes and eukaryotes: same function, different structure. Structure, 2002, vol. 10: 8-9.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a malonyl decarboxylase by replacemnt of the active-site cysteine with glutamine. Biochemistry, 1999, vol. 38: 11643-11650.*
Sunthankar P. et al., Synthesis of 5-azido-UDP-N-acetylhexosamine photoaffinity analogs and radiolabeled UDP-N-acetylhexosamines, Anal. Biochem., 1998, vol. 258, pp. 195-201.
Pastuszak, et al., "Identification of the GalNAc Kinase Amino Acid Sequence," The Journal of Biological Chemistry, vol. 271, No. 39, pp. 23653-23656, 1996.
Chen et al., Changing the donor cofactor of bovine alpha1, 3-galactosyltransferase by fusion with UDP-galactose 4-epimerase, J. Biol. Chem., 2000, vol. 275, No. 41, pp. 31594-31600.
Methods Enzymol., 1972, 28, pp. 271-277.
Heidlas et al., "Practical Enzyme-Based Syntheses of Uridine 5'-Diphosphogalactose and Uridine 5'-Diphospho-N-acetylgalactosamine on a Gram Scale," J. Org. Chem., 1992, 57, pp. 152-157.
Pastuszak et al., "Identification of the GalNAc Kinase Amino Acid Sequence," The Journal of Biological Chemistry, vol. 271, No. 39, 1996, pp. 23653-23656.
Strominger et al., "Uridine Diphosphoacetylglucosamine Pyrophosphorylase," The Journal of Biological Chemistry, vol. 234, No. 7, Jul. 1959, pp. 1822-1827.
Wang-Gillam, et al., "A 17-Amino Acid Insert Changes UDP-N-Acetylhexosamine Pyrophosphorylase Specificity from UDP-GalNAc to UDP-GlcNAc," The Journal of Biological Chemistry, vol. 273, No. 42, 1998, pp. 27055-27057.
Szumilo et al., "Purification to Homogeneity and Properties of UDP-GlcNAc (GalNAc) Pyrophosphorylase," vol. 271, No. 22, 1996, pp. 13147-13154.
Japanese Search Report dated Jan. 10, 2006.

* cited by examiner

*Primary Examiner* — Ganapathirama Raghu
(74) *Attorney, Agent, or Firm* — K&L Gates LLP

(57) ABSTRACT

The present invention provides a method for enzymatically producing uridine 5'-diphospho-N-acetylgalactosamine (UDP-GalNAc) (which is an important substrate for oligosaccharide synthesis) from uridine 5'-triphosphate (UTP) and N-acetylgalactosamine 1-phosphate (GalNAc 1-P), the method including using, as an enzyme, uridine 5'-diphospho-N-acetylglucosamine pyrophosphorylase (UDP-GlcNAc pyrophosphorylase) derived from a microorganism (exclusive of a pathogenic microorganism). The GalNAc 1-P employed can be prepared from N-acetylgalactosamine and a phosphate donor in a reaction system by use of N-acetylgalactosamine kinase. According to the present invention, uridine 5'-diphospho-N-acetylgalactosamine can be efficiently produced by use of a relatively inexpensive substrate.

5 Claims, 2 Drawing Sheets

SEQUENCE LISTING

```
<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: Primer for amplification of GALK2 gene

<400> SEQUENCE: 1
cggggatcca tggctacaga gagccctgct                                    30

<210> SEQ ID NO 2
<211> LENGTH: 30
<212> TYPE: DNA
<213> ORGANISM: Artificial Sequence
<220> FEATURE:
<223> OTHER INFORMATION: Primer for amplification of GALK2 gene

<400> SEQUENCE: 2
tacgtcgact taggcctcaa gcaaaaccaa                                    30

<210> SEQ ID NO 3
<211> LENGTH: 19
<212> TYPE: DNA
<213> ORGANISM: Artificial Sequence
<220> FEATURE:
<223> OTHER INFORMATION: Primer for amplification of glmU gene

<400> SEQUENCE: 3
gagcggataa caatttcac                                                19
```

```
<210> SEQ ID NO 4
<211> LENGTH: 30
<212> TYPE: DNA
<213> ORGANISM: Artificial Sequence
<220> FEATURE:
<223> OTHER INFORMATION: Primer for amplification of glmU gene

<400> SEQUENCE: 4
ccaggatccc tttttcttta ccggacgacg                                          30
```

METHOD OF PRODUCING URIDINE 5'-DIPHOSPHO-N-ACETYLGALACTOSAMINE

TECHNICAL FIELD

The present invention relates to a process for producing uridine 5'-diphospho-N-acetylgalactosamine (UDP-GalNAc), which is an important substrate for oligosaccharide synthesis.

BACKGROUND ART

Enzymatic synthesis of oligosaccharide is generally performed through either of the following two methods: a method utilizing reverse reaction of enzymatic hydrolysis of oligosaccharide, or a method employing glycosyltransferase. From the viewpoints of synthesis yield, and applicability to synthesis of an oligosaccharide having a complicated structure, a synthesis method employing glycosyltransferase is considered more advantageous than a method utilizing reverse reaction of enzymatic hydrolysis of oligosaccharide. An increase in production of various glycosyltransferases through recent development of recombinant DNA technology contributes to realization of this synthesis technique.

However, sugar nucleotides (i.e., sugar donors), which are employed in such a glycosyltransferase-employing synthesis method, remain expensive (exclusive to some sugar nucleotides), and are available only in small amounts of reagent level. As has been reported, UDP-GalNAc is synthesized through, for example, a method employing combination of an enzymatic process and chemical acetylation, in which galactosamine is used as a starting material.

However, this method poses, for example, the following problems: (A) the reaction has been limited to only a small scale (laboratory scale); (B) difficulty is encountered in preparing an enzyme employed; (C) acetylation of galactosamine requires an ATP regeneration system, resulting in low overall reaction yield; and (D) UDP-galactosamine, when remaining in the reaction mixture, would cause a problem in terms of separation thereof from UDP-GalNAc, which is a target product. Therefore, this method has not necessarily been considered practical (Methods Enzymol., 28, 271-277, (1972), J. Org. Chem., 57, 152-157, (1992)).

Meanwhile, there has been reported a method in which UDP-GalNAc is synthesized from uridine 5'-diphospho-N-acetylglucosamine (UDP-GlcNAc) by use of uridine 5'-diphospho-N-acetylglucosamine-4-epimerase (UDP-GlcNAc-4-epimerase) (WO 2002/050267). However, this method has the following problems: (A) only a small amount of UDP-GlcNAc-4-epimerase is present in animal tissues or microbial cells; and (B) since this enzymatic reaction employing UDP-GlcNAc-4-epimerase (which can be prepared through a recombinant DNA technique) is an equilibrium reaction, not only is conversion low, but also difficulty is encountered in separating UDP-GalNAc from UDP-GlcNAc (i.e., a substrate), which is not completely consumed and remains in the reaction mixture in a large amount. Therefore, this method remains problematic in practical use.

Patent Document 1: WO 2002/050267
Non-Patent Document 1: Methods Enzymol., 28, 271-277, (1972)
Non-Patent Document 2: J. Org. Chem., 57, 152-157, (1992)
Non-Patent Document 3: J. Biol. Chem. 271, 23653-23656, (1996)
Non-Patent Document 4: J. Biol. Chem. 234, 1822-1827 (1959)
Non-Patent Document 5: J. Biol. Chem. 273, 27055-27057 (1998)
Non-Patent Document 6: J. Biol. Chem. 271, 13147-13154 (1996)

DISCLOSURE OF THE INVENTION

In view of the foregoing, an objective of the present invention is to provide a practical method for enzymatically producing UDP-GalNAc efficiently by use of an inexpensive substrate.

The present inventors have conducted extensive studies on the biosynthetic pathway of UDP-GalNAc, and as a result have accomplished the present invention on the basis of the below-described findings.

Firstly, through experiments, the present inventors have found that uridine 5'-diphospho-N-acetylglucosamine pyrophosphorylase (UDP-GlcNAc pyrophosphorylase) derived from a nonpathogenic microorganism (other than *Staphylococcus aureus*) exhibits its intrinsic activity to catalyze the below-described conversion reaction (A), as well as activity to catalyze the below-described conversion reaction (B), although such nonpathogenic-microorganism-derived UDP-GlcNAc pyrophosphorylase has not been reported to have these catalytic activities (A) and (B), in contrast to the reports that UDP-GlcNAc pyrophosphorylase derived from pathogenic *Staphylococcus aureus*, human, or pig has these catalytic activities (A) and (B) (*J. Biol. Chem.* 234, 1822-1827 (1959), *J. Biol. Chem.* 273, 27055-27057 (1998), *J. Biol. Chem.* 271, 13147-13154 (1996)). The present inventors have also found that when, for example, UDP-GalNAc is synthesized from N-acetylgalactosamine 1-phosphate (GalNAc 1-P) and uridine 5'-triphosphate (UTP) by use of UDP-GlcNAc pyrophosphorylase derived from *Escherichia coli*, there can be solved a problem in terms of separation of UDP-GalNAc from other sugar nucleotides (e.g., UDP-GlcNAc and UDP-galactosamine), which is problematic in conventional methods.

(A) UDP-GlcNAc+pyrophosphate ⇔ UTP+GlcNAc 1-P
(B) UDP-GalNAc+pyrophosphate ⇔ UTP+GalNAc 1-P Subsequently, the present inventors have found that, during the course of studies on enzymatic phosphorylation of N-acetylgalactosamine (GalNAc), GalNAc 1-P, which is expensive and is not readily prepared chemically, can be enzymatically prepared from GalNAc by use of GalNAc kinase, which has been reported to be present in, for example, liver or kidney tissue of a human or pig (*J. Biol. Chem.* 271, 39, 23653-23656, (1996)).

The present inventors have also found that, although animal-derived N-acetylgalactosamine kinase has been difficult to produce in a system employing a microorganism (e.g., *Escherichia coli*) as a host, and thus the enzyme has been considered impossible to use in practice, when the GALK 2 gene encoding animal-derived N-acetylgalactosamine kinase is ligated with a 3'-downstream region of a gene encoding another microorganism-derived protein (e.g., *Escherichia coli* UDP-GlcNAc pyrophosphorylase) for producing the enzyme in the form of a fusion protein, animal-derived N-acetylgalactosamine kinase can be produced in an activated form in *Escherichia coli*.

The present inventors have also found that UDP-GalNAc can be synthesized from GalNAc and UTP by use of such animal-derived N-acetylgalactosamine kinase and microorganism-derived UDP-GlcNAc pyrophosphorylase, or by use of a fusion protein thereof, and that UDP-GalNAc can be synthesized from inexpensive uridine 5'-monophosphate (UMP) and GalNAc with N-acetylgalactosamine kinase and Escherichia coli UDP-GlcNAc pyrophosphorylase during phosphorylation of UMP and production of adenosine 5'-triphosphate (ATP) by yeast cells. The present invention has been accomplished on the basis of the aforementioned findings.

Accordingly, the present invention provides a method for enzymatically producing UDP-GalNAc from UTP and GalNAc 1-P, the method comprising using, as an enzyme, UDP-GlcNAc pyrophosphorylase derived from a microorganism (exclusive of a pathogenic microorganism).

In the UDP-GalNAc production method of the present invention, the aforementioned UDP-GlcNAc pyrophosphorylase is prepared through a recombinant DNA technique employing a microorganism-derived UDP-GlcNAc pyrophosphorylase gene.

In the UDP-GalNAc production method of the present invention, the aforementioned GalNAc 1-P is prepared from GalNAc and a phosphate donor in a reaction system by use of N-acetylgalactosamine kinase.

In the present invention, the aforementioned N-acetylgalactosamine kinase may be prepared through a recombinant DNA technique employing an animal-derived N-acetylgalactosamine kinase gene, may be prepared in the form of a fusion protein with a microorganism-derived protein through a recombinant DNA technique, or may be prepared in the form of a fusion protein with microorganism-derived UDP-GlcNAc pyrophosphorylase.

In the present invention, the aforementioned phosphate donor may be adenosine 5'-triphosphate (ATP), and ATP may be produced by yeast cells.

In the UDP-GalNAc production method of the present invention, UTP may be replaced by a UTP production/regeneration system employing cells of a microorganism or enzymes. For example, UTP may be replaced by a system of producing UTP from UMP using yeast cells.

In the present invention, the aforementioned microorganism-derived UDP-GlcNAc pyrophosphorylase gene may be an *Escherichia coli*-derived UDP-GlcNAc pyrophosphorylase gene (glmU). An enzyme which degrades pyrophosphate produced in a reaction system may be added during synthesis of UDP-GalNAc by use of the aforementioned UDP-GlcNAc pyrophosphorylase.

In the present invention, the aforementioned yeast cells may be cells of one or more yeast strains selected from the genera *Saccharomyces, Zygosaccharomyces, Candida, Torulopsis, Hansenula*, and *Debaryomyces*. The aforementioned yeast cells may be, for example, dry yeast cells. It is advantageous that an inorganic phosphate or a required energy source is added to a reaction employing the aforementioned yeast cells.

In the present invention, sodium fluoride may be added to prevent degradation of GalNAc 1-P prepared by use of the aforementioned N-acetylgalactosamine kinase.

According to the present invention, on the basis of the finding that microorganism-derived UDP-GlcNAc pyrophosphorylase has the activity to produce UDP-GalNAc from GalNAc 1-P and UTP, efficient production of UDP-GalNAc was first attained through phosphorylation of GalNAc and binding of UDP, pursued in a correlating manner, by use of this enzyme and animal-derived N-acetylgalactosamine kinase.

According to the present invention, since N-acetylgalactosamine kinase and UDP-GlcNAc pyrophosphorylase are produced in the form of fusion proteins, production of animal-derived N-acetylgalactosamine kinase has first been realized in *Escherichia coli*. That is, these two types of enzymes can be produced in one time, which facilitates preparation of the enzymes.

UDP-GalNAc can be effectively synthesized from inexpensive UMP and GalNAc through use of N-acetylgalactosamine kinase and microorganism-derived UDP-GlcNAc pyrophosphorylase while pursuing phosphorylation of UMP and production of ATP by yeast cells.

In the method of the present invention, since a sugar nucleotide other than UDP-GalNAc is scarcely produced, UDP-GalNAc (i.e., a target product) can be very easily isolated and purified from the resultant reaction mixture.

BEST MODE FOR CARRYING OUT THE INVENTION

Figure 1:
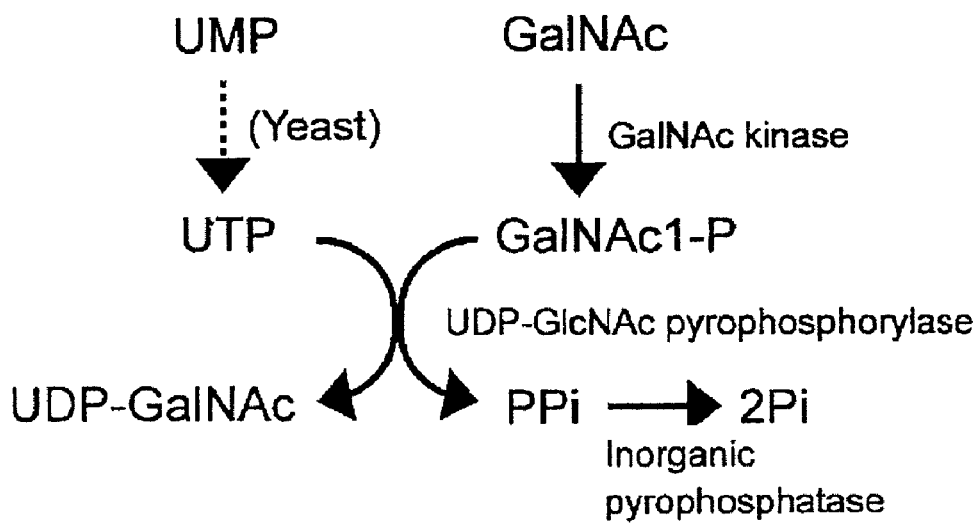
FIG. 1 shows a system of synthesizing UDP-GalNAc from GalNAc and UTP.

The present invention relates to a method for enzymatically producing UDP-GalNAc from UTP and GalNAc 1-P. A characteristic feature of the UDP-GalNAc production method resides in that microorganism-derived UDP-GlcNAc pyrophosphorylase is employed as an enzyme.

The UDP-GlcNAc pyrophosphorylase added to the reaction system may be derived from a non-pathogenic microorganism. Such an enzyme may be prepared through a so-called recombinant DNA technique, in which the gene for the enzyme is cloned, and expressed in a large amount in cells of a microorganism. Examples of the microorganism-derived UDP-GlcNAc pyrophosphorylase include those derived from microorganisms belonging to the genus *Escherichia* (Journal of Bacteriology, 175, 6150 (1993)), the genus *Saccharomyces* (Agricultural Biological Chemistry, 40, 2275 (1976)), and the genus *Neurospoa* (Can. J. Microbiology, 25, 1381 (1979)). Particularly, *Escherichia coli*-derived UDP-GlcNAc pyrophosphorylase is preferred.

No particular limitation is imposed on the form of such UDP-GlcNAc pyrophosphorylase, so long as the enzyme exhibits the aforementioned activity. Specific examples of the form of the enzyme include cells of a microorganism, a treated product of the cells, and an enzyme preparation obtained from the treated product.

Examples of the treated product of cells of a microorganism include a disrupted product or a cell-wall-denatured or cell-membrane-denatured product of cells obtained through treatment of the aforementioned microorganism cells by a generally employed technique, such as mechanical disruption (by a Waring blender, a French press, a homogenizer, a mortar, etc.), freeze-thawing, self-digestion, drying (freeze-drying, air-drying, etc.), treatment with an enzyme (e.g., lysozyme), ultrasonic treatment, or chemical treatment (acid treatment, alkali treatment, etc.).

Examples of the enzyme preparation include a crude enzyme or a purified enzyme prepared by subjecting, to a generally employed enzyme purification technique (e.g., salting-out, precipitation at an isoelectric point, precipitation with an organic solvent, dialysis, or any chromatographic technique), a fraction exhibiting the aforementioned enzymatic activity obtained from the above cell-treated product.

Specifically, UDP-GlcNAc pyrophosphorylase is prepared from cells of a microorganism as described below. Collected cells of a microorganism are disrupted through ultrasonic treatment, and the resultant disrupted cell preparation is subjected to centrifugation. The thus-obtained supernatant is treated with a chromatographic technique (e.g., ion-exchange chromatography or gel chromatography). The resultant fraction exhibiting UDP-GlcNAc pyrophosphorylase activity is concentrated and desalted, to thereby yield the target enzyme preparation.

Each of UTP and GalNAc 1-P, which are employed for reaction, may be prepared in the reaction system. For example, GalNAc 1-P may be prepared in the reaction system from GalNAc and a phosphate donor by use of N-acetylgalactosamine kinase.

N-Acetylgalactosamine kinase, which is employed for reaction, is contained in tissues of the kidney, liver, pancreas, lung, heart, aorta, brain, etc. of a mammal such as human, pig, or mouse; particularly in the kidney or liver in a large amount. N-Acetylgalactosamine kinase can be prepared from such tissues. No particular limitation is imposed on the form of N-acetylgalactosamine kinase added to the reaction system, so long as the enzyme exhibits the aforementioned activity. Specific examples of the form include a treated product of pig liver, and an enzyme preparation obtained from the treated product.

From the viewpoint of, for example, ease of preparation of the enzyme, preferably, N-acetylgalactosamine kinase is prepared through a so-called recombinant DNA technique, in which N-acetylgalactosamine kinase gene is cloned through a customary method, and expressed in a large amount in cells of a microorganism. In the case where animal-derived N-acetylgalactosamine kinase is prepared through a recombinant DNA technique by use of a microorganism as a host, when a customary process is employed, the target enzyme is not produced, or produced in only a small amount, which is not practical. Therefore, when a gene for animal-derived N-acetylgalactosamine kinase is ligated with a downstream region of a gene encoding a protein derived from the same microorganism as the host (e.g., *Escherichia coli* UDP-GlcNAc pyrophosphorylase), and is produced in the form of fusion protein, the animal-derived N-acetylgalactosamine kinase can be produced in a state where it exhibits activity in the host (e.g., *Escherichia coli*).

A technique for producing the aforementioned fusion protein (e.g., gene ligation, plasmid assembly, host transformation, or enzyme production) has already been well known in the art, and the fusion protein can be produced through a customary method as described below in Examples.

Similar to the case of UDP-GlcNAc pyrophosphorylase, no particular limitation is imposed on the form of N-acetylgalactosamine kinase added to reaction, so long as the enzyme exhibits the aforementioned activity. Specific examples of the form of the enzyme include cells of a microorganism, a treated product of the cells, and an enzyme preparation obtained from the treated product.

UTP can be prepared in the reaction system by use of a UTP production/regeneration system employing an enzyme or cells of a microorganism. Specifically, there may be employed a system of producing UTP from UMP, the system employing UMP and yeast cells. This production system will now be described (see FIG. 1).

No particular limitation is imposed on the yeast cells employed, so long as they are generally used for producing a sugar nucleotide. Specific examples include cells of yeast strains belonging to the genera *Saccharomyces, Zygosaccharomyces, Candida, Torulopsis, Hansenula*, and *Debaryomyces*. Such yeast cells may be live yeast cells or dry yeast cells. However, dry yeast cells are preferably employed, from the viewpoints of, for example, reaction yield and easy handling.

Preparation of UTP in the reaction system is not necessarily carried out by use of the aforementioned UTP production system employing UMP and yeast cells. For example, there may be employed a system of producing UTP from orotate using cells of a microorganism (Japanese Patent Application Laid-Open (kokai) No. H05-276974); or combination of a UTP production system and an ATP regeneration system using enzymes (specifically, a system in which UTP is produced by causing uridylate kinase and, if necessary, nucleoside diphosphate kinase to act on UMP, while ATP is regenerated by causing polyphosphate kinase, adenylate kinase, and polyphosphate to act on adenylic acid (AMP)).

Conditions for the enzymatic production of UDP-GalNAc somewhat vary with the enzyme and substrate employed therefor.

(1) Enzymatic production of UDP-GalNAc from UTP and GalNAc 1-P employing, as an enzyme, microorganism-derived UDP-GlcNAc pyrophosphorylase UTP and GalNAc 1-P employed for reaction may be commercially available ones, or may be prepared through application of a known method (*J. Am. Chem. Soc.*, 115, 2260-2267 (1993)). No particular limitation is imposed on the concentration of UTP or GalNAc 1-P employed, but the concentration is appropriately determined within a range of about 1 to about 200 mM (preferably, about 1 to about 100 mM).

UDP-GalNAc can be synthesized through, for example, the following procedure: UTP and GalNAc 1-P are added to a phosphate buffer (pH: about 6.0 to about 9.0); and the aforementioned UDP-GlcNAc pyrophosphorylase is added to the resultant reaction mixture in an amount of about 0.1 units/mL or more (preferably, about 0.5 to about 20.0 units/mL), followed by reaction in the presence of the enzyme at about 5 to about 30° C. (preferably, at about 5 to about 25° C.) for about 1 to about 70 hours with optional stirring.

The synthesis reaction of UDP-GalNAc by use of UDP-GlcNAc pyrophosphorylase is an equilibrium reaction. Therefore, in order to increase the synthesis yield of UDP-GalNAc, preferably, an enzyme which degrades pyrophosphate produced in the reaction system (e.g., pyrophosphatase) is added in an amount of 0.1 units/mL or more.

(2) Enzymatic production of UDP-GalNAc from UTP and GalNAc employing, as an enzyme(s), microorganism-derived UDP-GlcNAc pyrophosphorylase and animal-derived N-acetylgalactosamine kinase, or a fusion enzyme thereof UTP and GalNAc employed for reaction may be commercially available ones. No particular limitation is imposed on the concentration of UTP or GalNAc employed, but the concentration is appropriately determined within a range of about 1 to about 200 mM (preferably, about 1 to about 100 mM).

UDP-GalNAc can be synthesized through, for example, the following procedure: UTP and GalNAc are added to a phosphate buffer (pH: about 6.0 to about 9.0); and each of the aforementioned two enzymes, or a fusion enzyme thereof is added to the resultant reaction mixture in an amount of about 0.1 units/mL or more (preferably, about 0.5 to about 20.0 units/mL), followed by reaction in the presence of the enzyme (s) at about 5 to about 30° C. (preferably, at about 5 to about 25° C.) for about 1 to about 70 hours with optional stirring.

Preferably, an enzyme which degrades pyrophosphate (e.g., pyrophosphatase) is added in an amount of 0.1 units/mL or more in a manner similar to that described in (1) above, and sodium fluoride is further added in an amount of 1 mM or more so as to prevent degradation of GalNAc 1-P prepared by use of N-acetylgalactosamine kinase.

(3) Production of UDP-GalNAc from UMP and GalNAc employing a system of producing UTP from UMP by use of yeast cells, and employing, as an enzyme(s), microorganism-derived UDP-GlcNAc pyrophosphorylase and animal-derived N-acetylgalactosamine kinase, or a fusion enzyme thereof.

UMP and GalNAc employed for reaction may be commercially available ones. No particular limitation is imposed on the concentration of UMP or GalNAc employed, but the concentration is appropriately determined within a range of about 1 to about 200 mM (preferably, about 10 to about 50 mM).

UDP-GalNAc can be synthesized through, for example, the following procedure: UMP and GalNAc are added to a phosphate buffer (pH: about 6.0 to about 9.0); each of the aforementioned two enzymes, or a fusion enzyme thereof is added to the resultant reaction mixture in an amount of about 0.1 units/mL or more (preferably, about 0.5 to about 20.0 units/mL); and yeast cells are added thereto in an amount of 1 to 10% (w/v), followed by reaction in the presence of the enzyme(s) and the yeast cells at about 5 to about 30° C. for about 1 to about 70 hours with optional stirring.

Preferably, an inorganic phosphate and an energy source are added to the aforementioned reaction system. The inorganic phosphate (e.g., potassium phosphate) may be employed as it is, but is preferably employed in the form of phosphate buffer. Examples of the energy source which may be employed include sugars such as glucose and fructose, and organic acids such as acetic acid and citric acid. No particular limitation is imposed on the concentration of the inorganic phosphate or energy source employed, but the concentration is appropriately determined within a range of about 10 to about 1,000 mM (preferably, about 100 to about 500 mM).

Unlike the cases of the enzymatic reactions described above in (1) and (2), the aforementioned reaction system does not require addition of an enzyme which degrades pyrophosphate, or a fluoride salt (e.g., sodium fluoride) for preventing degradation of GalNAc 1-P.

The thus-produced UDP-GalNAc can be isolated and purified through generally employed sugar nucleotide isolation/purification means (e.g., ion-exchange chromatography, adsorption chromatography, or salting-out).

EXAMPLES

The present invention will next be described in detail by way of Examples, which should not be construed as limiting the invention thereto. Throughout the Examples, UDP-GalNAc in reaction mixtures was quantitatively determined through HPLC. Specifically, separation was carried out by use of an ODS-AQ312 column (product of YMC Co.) and a 0.5 M monopotassium phosphate solution as an eluent. All procedures, including preparation of DNA, digestion with restriction enzymes, ligation of DNA by T4 DNA ligase, and transformation of *Escherichia coli*, were performed according to "Molecular Cloning" (edited by Maniatis, et al., Cold Spring Harbor Laboratory, Cold Spring Harbor, N.Y. (1982)).

Restriction enzymes, ExTaq DNA polymerase, and T4 DNA ligase were obtained from Takara Bio Inc.

Example 1

(1) Cloning of GALK2 Gene Encoding Human Kidney-Derived N-Acetylgalactosamine Kinase By using a human kidney-derived cDNA library (available from Clontech) as a template, the following two primer DNAs were synthesized through a customary method, and human kidney GALK2 gene (Submitted to NCBI, Accession No. NM 002044) was amplified through PCR.

Primer (A): 5'-CGGGGATCCATGGCTACAGAGAGC-CCTGCT-3'
Primer (B): 5'-TACGTCGACTTAGGCCTCAAG-CAAAACCAA-3'

PCR amplification of the GALK2 gene was performed by means of a DNA Thermal Cycler Dice (product of Takara Bio Inc.) through 30 cycles of treatment, each cycle consisting of the steps of thermal denaturation (94° C., one minute), annealing (59° C., one minute), and elongation (72° C., two minutes), of a reaction mixture (1001 µL) containing 50 mM potassium chloride, 10 mM Tris-HCl (pH 8.3), 1.5 mM magnesium chloride, 0.001% gelatin, 0.2 mM dATP, 0.2 mM dGTP, 0.2 mM dCTP, 0.2 mM dTTP, template DNA (0.1 ng), primer DNAs (A) and (B) (0.2 µM each), and ExTaq DNA polymerase (2.5 units).

After amplification of the gene, the resultant DNA was separated through agarose gel electrophoresis according to the method of the literature ("Molecular Cloning," referred to above), to thereby purify DNA fragments of 1.4 kb. The DNA was digested with restriction enzymes BamHI and SalI, and ligated with plasmid pMAL-c2x (obtained from New England Biolabs)—which had been digested with the same restriction enzymes BamHI and SalI—by use of T4 DNA ligase. *Escherichia coli* K12 strain JM109 (obtained from Takara Bio Inc.) was transformed by use of the ligation mixture, and plasmid pMAL-hGLK2 was isolated from the thus-obtained ampicillin-resistant transformant. The plasmid pMAL-hGLK2 is a product obtained by inserting of a BamHI-SalI DNA fragment containing the human kidney GALK2 structural gene into the BamHI-SalI cleavage sites at downstream of the 3'-end of the a maltose binding protein gene.

(2) Preparation of Human Kidney GALK2 Gene Product

*Escherichia coli* JM109 harboring plasmid pMAL-hGLK2 was inoculated into a culture medium (2% peptone, 1% yeast extract, 0.5% NaCl, 0.1% glucose) (100 mL) containing 100 µg/mL of ampicillin, followed by shaking culture at 37° C. When the number of cells reached $4 \times 10^8$ cells/mL, IPTG was added to the culture broth so that the final concentration thereof was 0, 0.01, 0.1, or 1.0 mM, followed by further shaking culture at 25° C. for 20 hours. After completion of shaking culture, the resultant cells were collected through centrifugation (4° C., 9,000×g, 10 minutes), and then suspended in a buffer (50 mM potassium phosphate (pH 7.5)) (20 mL). The resultant suspension was subjected to ultrasonic treatment under ice cooling by means of an ultrasonic cell disruptor (Sonifier (model 450), product of Branson) (50 W, two minutes, three times), followed by centrifugation (4° C., 12,000×g, 20 minutes) for collection of a soluble fraction (supernatant).

The thus-obtained supernatant fraction was provided as an enzyme sample, and N-acetylgalactosamine kinase activity of the enzyme sample was determined. The results are shown in the following table.

TABLE 1

| Bacterium/plasmid | IPTG concentration (mM) | N-Acetylgalactosamine kinase activity (units/mg-protein) |
|---|---|---|
| JM109/pMAL-hGLK2 | 0 | <0.01 |
| | 0.01 | 0.04 |
| | 0.1 | 0.24 |
| | 1.0 | 0.25 |

In order to determine N-acetylgalactosamine kinase activity, activity of phosphorylation of ATP and GalNAc into GalNAc 1-P was determined/calculated through the below-described method. Specifically, an N-acetylgalactosamine kinase sample is added to 100 mM Tris-HCl buffer (pH 7.5), 10 mM magnesium chloride, 5 mM GalNAc, 5 mM ATP.3Na, and 5 mM sodium fluoride, followed by reaction at 37° C. for 10 minutes. Reaction is stopped through five-minute boiling of the reaction mixture, and the resultant reaction mixture is subjected to analysis by means of a sugar analyzer HPAEC-CD (High-performance anion-exchange chromatography coupled with conductimetric detection). Separation is performed by use of Carbopac PA1 column (4×250 mm, product of Dionex) and, as an eluent, a mixture of (A) 0.1 M NaOH solution and (B) 0.1 M NaOH, 0.5 M sodium acetate solution (concentration gradient: 0 to 15 min: B=1% to 50%, 15 to 20 min: B=100%). The amount of GalNAc 1-P produced in the reaction mixture is calculated on the basis of the results of HPAEC-CD analysis, and the activity corresponding to production of 11 μmole of GalNAc1-P at 37° C. for one minute is defined as one unit.

(3) Preparation of UDP-GlcNAc Pyrophosphorylase

*Escherichia coli* JM109 [pTrc-glmU] which had been prepared from chromosomal DNA of *Escherichia coli* (IFO3972=NBRC3972) through the method of the literature (*Biosci. Biotechnol. Biochem.*, 64 (2), 386-392 (2000)) was inoculated into a 2×YT culture medium (10 mL) containing 100 μg/mL of ampicillin (Methods Enzymol., 153, 3-11, (1987)), followed by culturing at 37° C. overnight. The resultant product was inoculated into a 2×YT culture medium (500 mL) containing 100 μg/mL of ampicillin, followed by culturing at 37° C. for two hours. Thereafter, IPTG was added to the culture medium so that the final concentration thereof was 0.1 mM, followed by culturing at 37° C. overnight. After completion of culturing, the resultant cells were collected through centrifugation (4° C., 9,000×g, 20 minutes). The thus-collected cells were suspended in 50 mM Tris-HCl (pH 7.5), and then disrupted by means of an ultrasonic cell disruptor (Sonifier (model 450), product of Branson) (50 W, two minutes, three times), followed by centrifugation (4° C., 15,000 rpm, 20 minutes) for collection of a soluble fraction (supernatant).

The thus-obtained supernatant fraction was provided as an enzyme sample, and UDP-GlcNAc pyrophosphorylase activity of the enzyme sample was determined. The results are shown in Table 2 together with those of the reference bacterium (*Escherichia coli* JM109 harboring pTrc99A).

TABLE 2

| Bacterium/plasmid | UDP-GlcNAc pyrophosphorylase (units/mg-protein) |
|---|---|
| JM109/pTrc99A | 0.19 |
| JM109/pTrc-glmU | 30.97 |

In order to determine UDP-GlcNAc pyrophosphorylase activity, activity of degradation of UDP-GlcNAc and pyrophosphate to N-acetylglucosamine 1-phosphate and UTP was determined/calculated through the method described in Biosci. Biotechnol. Biochem., 64 (2), 386-392 (2000). Specifically, a UDP-GlcNAc pyrophosphorylase sample is added to 50 mM Tris-HCl buffer (pH 7.5), 5 mM magnesium chloride, 3 mM sodium pyrophosphate, and 1 mM UDP-GlcNAc, followed by reaction at 37° C. for five minutes. Meanwhile, a similar reaction is performed using water in place of a sodium pyrophosphate solution, and the resultant product is provided as a control.

Reaction is stopped through five-minute boiling of the reaction mixture, and the resultant reaction mixture is subjected to HPLC analysis. Separation is performed by use of an ODS-AQ312 column (product of YMC Co.) and a 0.5 M monopotassium phosphate solution as an eluent. The amount of UTP produced in the reaction mixture is calculated on the basis of the results of HPLC analysis, and the activity corresponding to production of 11 μmole of UTP at 37° C. for one minute is defined as one unit.

(4) Enzymatic Synthesis of UDP-GalNAc by Use of *Escherichia coli* UDP-GlcNAc Pyrophosphorylase The UDP-GlcNAc pyrophosphorylase solution prepared above in (3) and having a predetermined activity (4.8 units) was added to a solution (0.5 mL) containing 50 mM Tris-HCl buffer (pH 7.5), 5 mM magnesium chloride, 1 mM 5'-UTP.3Na, and 1 mM GalNAc 1-P, followed by reaction at 37° C. In the middle of the reaction, an appropriate amount of the reaction mixture was collected, and then boiled for five minutes, followed by centrifugation. The resultant supernatant was subjected to HPLC analysis.

Analysis of the reaction mixture after initiation of the reaction showed that 0.33 mM UDP-GalNAc was synthesized from 1 mM UTP and 1 mM GalNAc 1-phosphate. Analysis also showed that, through addition of inorganic pyrophosphatase (product of Sigma) to the reaction mixture, the equilibrium was shifted toward the UDP-GalNAc synthesis side, and the synthesis yield was increased (by about 60%).

Example 2

(1) Synthesis of UDP-GalNAc by Use of Human N-Acetylgalactosamine Kinase and *Escherichia coli* UDP-GlcNAc Pyrophosphorylase The N-acetylgalactosamine kinase solution (0.094 units) and UDP-GlcNAc pyrophosphorylase solution (4.4 units) prepared above in Example 1, each having a predetermined activity, and inorganic pyrophosphatase (product of Sigma, 0.5 units) were added to a solution (0.2 mL) containing 100 mM Tris-HCl buffer (pH 7.5), 10 mM magnesium chloride, 5 mM 5'-UTP.3Na, 5 mM GalNAc, 5 mM 5'-ATP.3Na, and 5 mM sodium fluoride, followed by reaction at 37° C.

In the middle of the reaction, an appropriate amount of the reaction mixture was collected, and then boiled for five minutes, followed by centrifugation. The resultant supernatant was subjected to HPLC analysis. Analysis of the reaction mixture four hours after initiation of the reaction showed that 3.2 mM UDP-GalNAc was synthesized in the presence of N-acetylgalactosamine kinase, UDP-GlcNAc pyrophosphorylase, and inorganic pyrophosphatase. Reaction in the presence of UDP-GlcNAc pyrophosphorylase and inorganic pyrophosphatase but in the absence of N-acetylgalactosamine kinase did not produce UDP-GalNAc.

Example 3

Figure 2:
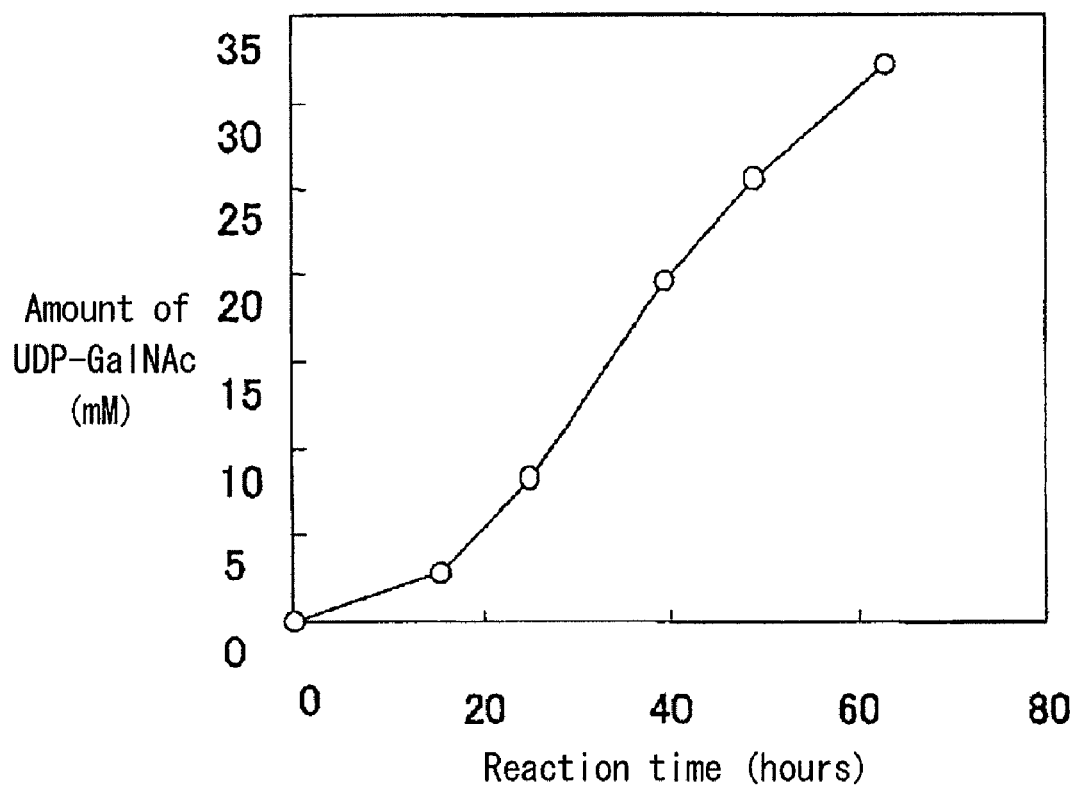
FIG. 2 shows a time-course change in amount of UDP-GalNAc produced in the presence of human kidney-derived N-acetylgalactosamine kinase and *Escherichia coli* UDP-GlcNAc pyrophosphorylase.

(1) Synthesis of UDP-GalNAc by Use of Dry Yeast, Human N-Acetylgalactosamine Kinase, and Escherichia coli UDP-GlcNAc Pyrophosphorylase The recombinant enzyme prepared in Example 1 (N-acetylgalactosamine kinase: 0.32 units, UDP-GlcNAc pyrophosphorylase: 10.4 units) was added to a solution (1 mL) containing 200 mM glucose, 50 mM GalNAc, 50 mM UMP, 200 mM potassium phosphate (pH 8.0), 20 mM magnesium chloride, and 3% (w/v) dry baker's yeast (Oriental Yeast Co., Ltd.), followed by reaction at 26° C. with stirring at a speed of 300 rpm. A 2M glucose solution (0.1 mL) was added to the reaction mixture 16 hours, 24 hours, 40 hours, and 48 hours after initiation of the reaction. FIG. 2 shows the results of time-course analysis of the reaction mixture. The amount of accumulated UDP-GalNAc reached 32 mM through 49-hour reaction.

Example 4

In Example 2 or 3, reaction was performed by use of two types of enzymes. In contrast, in Example 4, UDP-GalNAc was synthesized by use of a fusion protein produced from two types of enzymes.

(1) Fusion of Escherichia coli UDP-GlcNAc Pyrophosphorylase and Human Kidney-Derived N-Acetylgalactosamine Kinase By using, as a template, plasmid pTrc-glmU for expression of Escherichia coli UDP-GlcNAc pyrophosphorylase gene, the following two primer DNAs were synthesized through a customary method, and a glmU-gene-containing DNA fragment was amplified through PCR.

Primer (C): 5'-GAGCGGATAACAATTTCAC-3'
Primer (D): 5'-CCAGGATCCCTTTTTCTTTACCGGACGACG-3'

PCR amplification of the glmU-gene-containing DNA fragment was performed by means of a DNA Thermal Cycler Dice (product of Takara Bio Inc.) through 30 cycles of treatment, each cycle consisting of the steps of thermal denaturation (94° C., one minute), annealing (64° C., one minute), and elongation (72° C., two minutes), of a reaction mixture (100 μL) containing 50 mM potassium chloride, 10 mM Tris-HCl (pH 8.3), 1.5 mM magnesium chloride, 0.001% gelatin, 0.2 mM dATP, 0.2 mM dGTP, 0.2 mM dCTP, 0.2 mM dTTP, template DNA (0.1 ng), primer DNAs (A) and (B) (0.2 μM each), and ExTaq DNA polymerase (2.5 units).

After amplification of the DNA fragment, the resultant DNA was separated through agarose gel electrophoresis according to the method of the literature ("Molecular Cloning," referred to above), to thereby purify DNA fragments of 1.4 kb. The DNA was digested with restriction enzymes EcoRI and BamHI, and ligated with plasmid pTrc99A (obtained from Pharmacia)—which had been digested with the same restriction enzymes EcoRI and BamHI—by use of T4 DNA ligase. Escherichia coli K12 strain JM109 (obtained from Takara Bio Inc.) was transformed by use of the ligation mixture, and plasmid pTrc-glmU3 was isolated from the thus-obtained ampicillin-resistant transformant. The glmU gene of pTrc-glmU3 lacks a stop codon, but instead contains an inserted BamHI recognition site.

Subsequently, pTrc-hGLK2 was digested with restriction enzymes BamHI and SalI, to thereby isolate and purify DNA fragments of 1.4 kb. The DNA was ligated with plasmid pTrc-glmU3—which had been digested with the same restriction enzymes BamHI and SalI—by use of T4 DNA ligase. Escherichia coli JM109 was transformed by use of the ligation mixture, and plasmid pTrc-glmU.hGLK2 was isolated from the thus-obtained ampicillin-resistant transformant. The plasmid pTrc-glmU.hGLK2 is a product obtained by ligating the hGLK2 gene with a 3'-downstream region of the glmU gene so that the frames of the genes match each other. Subsequently, pTrc-glmU.hGLK2 was digested with restriction enzymes SadI and SalI, to thereby isolate and purify DNA fragments of 1.4 kb. The DNA was ligated with plasmid pTrc12-6—which had been digested with the same restriction enzymes SadI and SalI—by use of T4 DNA ligase. Escherichia coli DH1 strain (ATCC 33849) was transformed by use of the ligation mixture, and plasmid p12-6-glmU.hGLK2 was isolated from the thus-obtained kanamycin-resistant transformant.

The plasmid pTrc12-6 is assembled from plasmid vector πAG1 (deposit number of Escherichia coli K-12 strain TNC111 harboring plasmid vector πAG1: FERM BP-6901: deposited on Sep. 30, 1999) and expression plasmid pTrc99A. The plasmid pTrc12-6 completely lacks the β-lactamase gene of pTrc99A (position 567-1816 by deleted), but has a Tn903-derived kanamycin-resistant gene inserted in the deletion site (Japanese Patent Application Laid-Open (kokai) No. 2001-103973).

(2) Preparation of Fusion Protein of Escherichia coli glmU Gene Product and Human Kidney GALK2 Gene Product Escherichia coli DH1 strain harboring plasmid p12-6-glmU.hGLK2 was inoculated into a culture medium (2% peptone, 1% yeast extract, 0.5% NaCl, 0.1% glucose) (50 mL) containing 100 μg/mL of kanamycin, followed by shaking culture at 37° C. When the number of cells reached $4 \times 10^8$ cells/mL, IPTG was added to the culture broth so that the final concentration thereof was 0.1 mM, followed by further shaking culture at 25° C. for 20 hours. After completion of shaking culture, the resultant cells were collected through centrifugation (4° C., 9,000×g, 10 minutes), and then suspended in a buffer (50 mM potassium phosphate (pH 7.5)) (20 mL). The cells were disrupted through ultrasonic treatment under ice cooling, and the cellular residue was removed through additional centrifugation (4° C., 12,000×g, 10 minutes).

The thus-obtained supernatant fraction was provided as an enzyme sample. UDP-GlcNAc pyrophosphorylase activity and N-acetylgalactosamine kinase activity of the enzyme sample were determined through the method described in Example 1. The results are shown in Table 3.

TABLE 3

| Bacterium/plasmid | UDP-GlcNAc pyrophosphorylase activity (units/mg-protein) | N-Acetylgalactosamine kinase activity (units/mg-protein) |
|---|---|---|
| DH1/pTrc12-6 | 0.16 | <0.01 |
| DH1/p12-6-glmU · hGLK2 | 9.11 | 0.18 |

(3) Synthesis of UDP-GalNAc by Use of Fusion Protein

UDP-GalNAc was synthesized by use of the above-obtained fusion enzyme sample. Specifically, the recombinant fusion enzyme solution (N-acetylgalactosamine kinase: 1.75 units, UDP-GlcNAc pyrophosphorylase: 88.9 units) was added to a solution (2.5 mL) containing 200 mM glucose, 50 mM GalNAc, 28 mM UMP, 200 mM potassium phosphate (pH 8.0), 20 mM magnesium chloride, and 3% (w/v) dry baker's yeast (Oriental Yeast Co., Ltd.), followed by reaction at 27° C. with stirring at 100 rpm. Glucose (0.09 g) was added to the reaction mixture 14 hours, 24 hours, and 40 hours after initiation of the reaction. A 0.5 M UMP solution (110 μL) was added to the reaction mixture 24 hours after initiation of the reaction.

Figure 3:
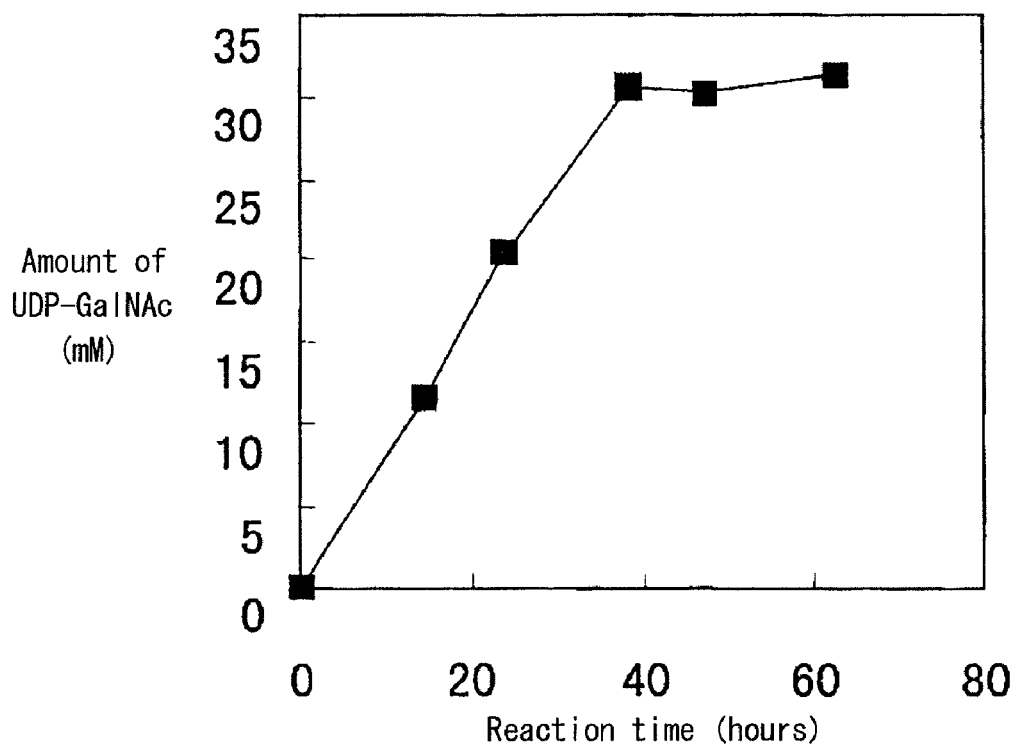
FIG. 3 shows a time-course change in amount of UDP-GalNAc produced by use of a fusion protein of human kidney-derived N-acetylgalactosamine kinase and *Escherichia coli* UDP-GlcNAc pyrophosphorylase.

FIG. 3 shows the results of time-course analysis of the reaction mixture. Similar to the case where these enzymes were prepared separately and mixed upon use, when the fusion protein was employed, UDP-GalNAc was synthesized, and the amount of UDP-GalNAc reached 30 mM through 40-hour reaction.

(4) Preparation of Fusion Protein of *Escherichia coli* glmU Gene Product and Human Kidney GALK2 Gene Product (Scale-Up)

*Escherichia coli* DH1 strain harboring plasmid p12-6-glmU.hGLK2 was inoculated into a culture medium (2% peptone, 1% yeast extract, 0.5% NaCl, 0.1% glucose) (3 mL) containing 100 μg/mL of kanamycin, followed by shaking culture at 37° C. overnight. Subsequently, the entirety of the resultant culture broth was inoculated into the aforementioned culture medium (125 mL), followed by shaking culture at 37° C. for 8 to 11 hours. Subsequently, the entirety of the resultant culture broth was inoculated into the aforementioned culture medium (5 L), followed by culturing under the following conditions: 37° C., aeration rate: 1.0 vvm, stirring blade rotation speed: 300 rpm. When the number of cells reached $4 \times 10^8$ cells/mL, IPTG was added to the culture broth so that the final concentration thereof was 0.1 mM, followed by further culturing at 28° C. for 14 hours. After completion of culturing, the resultant cells were collected through centrifugation (9,000×g, 10 minutes), and then suspended in a buffer (50 mM potassium phosphate (pH 7.5)) (500 mL). The cells were disrupted through ultrasonic treatment under ice cooling, and then the cellular residue was removed through centrifugation (12,000×g, 10 minutes).

The thus-obtained supernatant fraction was provided as an enzyme sample. UDP-GlcNAc pyrophosphorylase activity of the enzyme sample was determined through the method described in Example 1. The activity was found to be 9.50 units/mg-protein.

(5) Synthesis of UDP-GalNAc (Scale-Up)

Synthesis of UDP-GalNAc by use of the fusion enzyme sample was carried out on a large scale in a jar fermenter. Specifically, 200 mM glucose, 50 mM N-acetylgalactosamine, 28 mM UMP, 200 mM potassium phosphate (pH 8.0), 20 mM magnesium chloride, 3% (w/v) dry baker's yeast (Oriental Yeast Co., Ltd.), and the aforementioned recombinant fusion enzyme solution (525,000 units as UDP-GlcNAc pyrophosphorylase activity) were added to the fermenter, and the resultant mixture was filled up to 1,500 mL, followed by reaction under the following conditions: 27° C., aeration rate: 0.1 vvm, stirring blade rotation speed: 150 rpm. Glucose (54 g) was added to the reaction mixture 14 hours, 24 hours, and 38 hours after initiation of the reaction. A 0.5 M UMP solution (66 mL) was added to the reaction mixture 24 hours after initiation of the reaction.

Figure 4:
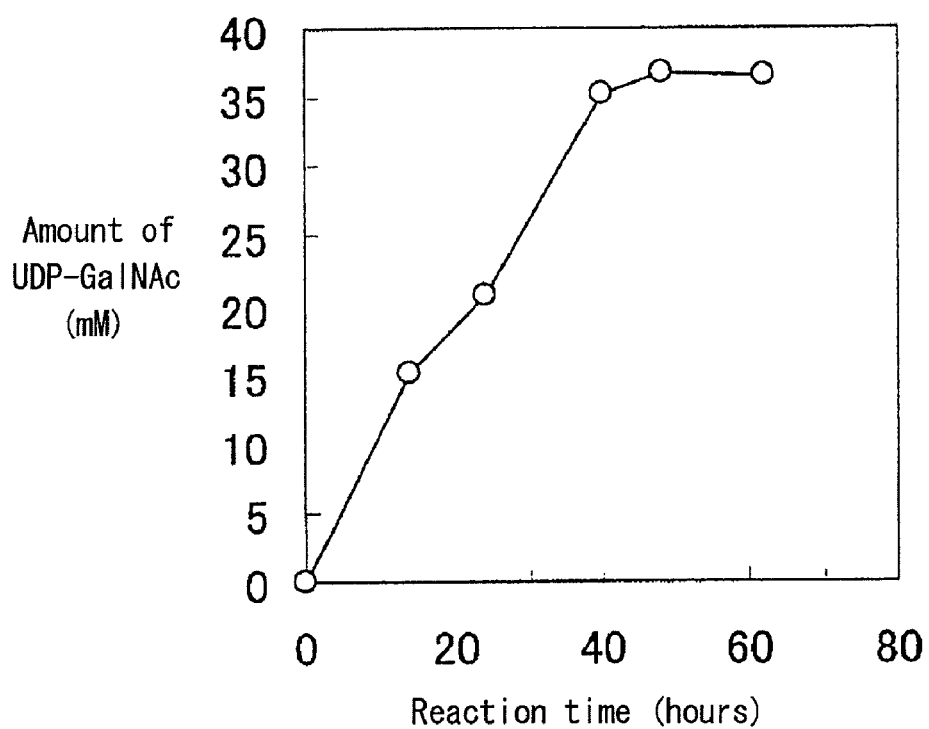
FIG. 4 shows a time-course change in amount of UDP-GalNAc produced through synthesis reaction in a jar fermenter.

FIG. 4 shows the results of time-course analysis of the reaction mixture. Even in the case of reaction in the jar fermenter, UDP-GalNAc was synthesized, and the amount of UDP-GalNAc reached 35 mM through 40-hour reaction.

The invention claimed is:

1. A method for enzymatically producing uridine 5'-diphospho-N-acetylgalactosamine (UDP-GalNAc) from uridine 5'-monophosphate (UMP) and N-acetylgalactosamine (GalNAc), the method comprising the steps of:

preparing a fusion gene by ligating a gene that encodes for human GalNAc kinase to a 3'-downstream region of a gene that encodes for *Escherichia coli* uridine 5'-diphospho-N-acetylglucosamine (UDP-GlcNAc) pyrophosphorylase, wherein the gene that encodes for human GalNAc kinase is GALK2 and wherein the gene that encodes for *Escherichia coli* UDP-GlcNAc pyrophosphorylase is glmU;

expressing a fusion protein comprising the enzymes Gal-NAc kinase and UDP-GlcNAc pyrophosphorylase through transformation of the fusion gene to *Escherichia coli*;

producing N-acetylgalactosamine 1-P (GalNAc 1-P) by enzymatic phosphorylation of GalNAc in a reaction mixture containing the expressed fusion protein and yeast cells having an adenosine 5'-triphosphate (ATP) and uridine 5'-triphosphate (UTP) production/regeneration system;

producing UTP by enzymatic phosphorylation of UMP employing the UTP production/regeneration system of the yeast cells;

enzymatically producing the UDP-GalNAc from the Gal-NAc 1-P and UTP; and isolating and purifying the UDP-GalNAc from the reaction mixture.

2. The method according to claim 1, wherein the yeast cells are cells of one or more yeast strains selected from the genera *Sacchoaromyces, Zygosaccharomyces, Candida, Torulopsis, Hansenula*, or *Debaryomyces*.

3. The method according to claim 1, wherein the yeast cells are dry yeast cells.

4. The method according to claim 1, wherein an inorganic phosphate is added to the reaction employing the yeast cells.

5. The method according to claim 1, wherein a required energy source is added to the reaction employing the yeast cells.

* * * * *